United States Patent
Lee et al.

(10) Patent No.: US 10,421,780 B2
(45) Date of Patent: Sep. 24, 2019

(54) PEPTIDE FOR TARGETING AUTOPHAGIC CELLS AND USE THEREOF

(71) Applicant: Kyungpook National University Industry-Academic Cooperation Foundation, Daegu (KR)

(72) Inventors: Byung-Heon Lee, Daegu (KR); Bodhraj Acharya, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 0 days.

(21) Appl. No.: 15/687,219

(22) Filed: Aug. 25, 2017

(65) Prior Publication Data

US 2018/0002380 A1    Jan. 4, 2018

Related U.S. Application Data

(63) Continuation of application No. PCT/KR2016/001943, filed on Feb. 26, 2016.

(30) Foreign Application Priority Data

Feb. 27, 2015  (KR) .................. 10-2015-0028567

(51) Int. Cl.
| | |
|---|---|
| *A61K 31/436* | (2006.01) |
| *A61K 47/50* | (2017.01) |
| *A61K 47/62* | (2017.01) |
| *A61K 49/00* | (2006.01) |
| *C07K 19/00* | (2006.01) |
| *C07K 7/06* | (2006.01) |
| *C07K 7/08* | (2006.01) |
| *G01N 33/58* | (2006.01) |
| *A61K 31/4706* | (2006.01) |
| *G01N 33/569* | (2006.01) |

(52) U.S. Cl.
CPC .............. *C07K 7/06* (2013.01); *A61K 31/436* (2013.01); *A61K 31/4706* (2013.01); *A61K 47/50* (2017.08); *A61K 47/62* (2017.08); *A61K 49/00* (2013.01); *G01N 33/56966* (2013.01); *G01N 33/58* (2013.01); *C07K 2319/035* (2013.01)

(58) Field of Classification Search
CPC .. A61K 31/436; A61K 31/4706; A61K 47/50; A61K 47/62; A61K 49/00; C07K 19/00; C07K 2139/035; C07K 7/06; C07K 7/08; G01N 33/56966; G01N 33/58
USPC .......... 514/21.5, 21.6; 530/327, 300
See application file for complete search history.

(56) References Cited

U.S. PATENT DOCUMENTS 9,771,393 B2 * 9/2017 Choi ................. C07K 7/06
2012/0042398 A1 2/2012 Gottlieb et al.

FOREIGN PATENT DOCUMENTS

| EP | 2466294 B1 | 7/2014 |
|---|---|---|
| KR | 10-2014-0130367 A | 11/2014 |
| WO | WO 2012/057640 A1 | 5/2012 |

OTHER PUBLICATIONS

Stapleton et al, "A *Drosophila* full-length cDNA resource," Genome Biology, 2002, 3(12): 1-8.*
Q8T455 from UniProt, pp. 1-5. Integrated into UniProtKB/TrEMBL Jun. 1, 2002.*
Acharya et al. (2013) In vivo imaging of myocardial cell death using a peptide probe and assessment of long-term heart function. J Control Release 172:367-373.
Jimenez et al. (2014) Autophagy and mitophagy in the myocardium: therapeutic potential and concerns. Br J Pharmacol 171:1907-1916.
Matsui et al. (2007) Distinct roles of autophagy in the heart during ischemia and reperfusion: Roles of AMP-activated protein kinase and Beclin1 in mediating autophagy. CircRes 100(6):914-22.
Mizushima et al. (Mar. 2004) In vivo analysis of autophagy in response to nutrient starvation using transgenic mice expressing a fluorescent autophagosome marker. Molecular Biology of the Cell 15(3):1101-1111.
Mizushima et al. (Feb. 2010) Methods in mammalian autophagy research. Cell 140(3):313-326.
Nishida et al. (2009) The Role of Autophagy in the Heart. Cell Death Differ 16:31-38.
Sciarretta et al. (2011) Is autophagy in response to ischemia and reperfusion protective or detrimental for the heart? Pediatr Cardiol 32(3):275-281.
Tian et al. (2010) In vivo imaging of autophagy in a mouse stroke model. Autophagy 6(8):1107-1114.

(Continued)

*Primary Examiner* — Julie Ha
(74) *Attorney, Agent, or Firm* — Jenkins, Wilson Taylor & Hunt, P.A.

(57) ABSTRACT

An autophagic cell targeted peptide and its use are described. More particularly, a polypeptide comprising an amino acid sequence represented by the general formula (I) and specifically binding to an autophagic cell and a composition for detecting autophagic cells comprising the same as an active ingredient are described. Also described are a drug delivery composition containing the same peptide as an active ingredient and a composition for imaging comprising the same peptide as an active ingredient. The peptide specifically binds to the cell membrane of autophagic cells and can be applied to various kinds of tissues and cells. The detection and imaging effect of autophagy is remarkable in vitro and in vivo.

5 Claims, 10 Drawing Sheets
(9 of 10 Drawing Sheet(s) Filed in Color)
Specification includes a Sequence Listing.

(56) References Cited

OTHER PUBLICATIONS

Degtyarev et al., "Novel Quantitative Autophagy Analysis by Organelle Flow Cytometry after Cell Sonication," PLoS One, vol. 9, No. 1, e87707, pp. 1-14 (2014).
International Search Report corresponding to Internation Application Serial No. PCT/KR2016/001943 dated May 20, 2016.
IPRP and Written Opinion corresponding to Internation Application Serial No. PCT/KR2016/001943 dated Aug. 29, 2017.
Kepp et al., "Cell death assays for drug discovery," Nat Rev Drug Discov, vol. 10, No. 3, pp. 221-237 (2011).
Matus et al., "A New Method to Measure Autophagy Flux in the Nervous System," Autophagy, vol. 10, No. 4, pp. 710-714 (2014).

\* cited by examiner

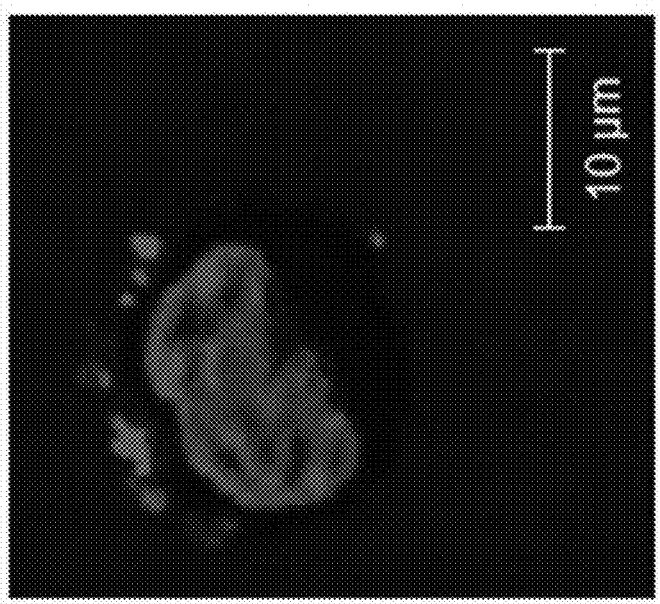
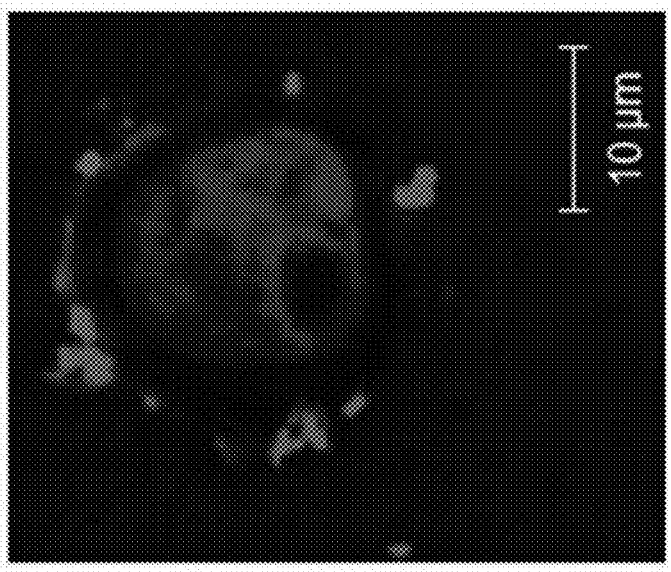

Fig 10
tumor : FPR675-CQQTKNYYC
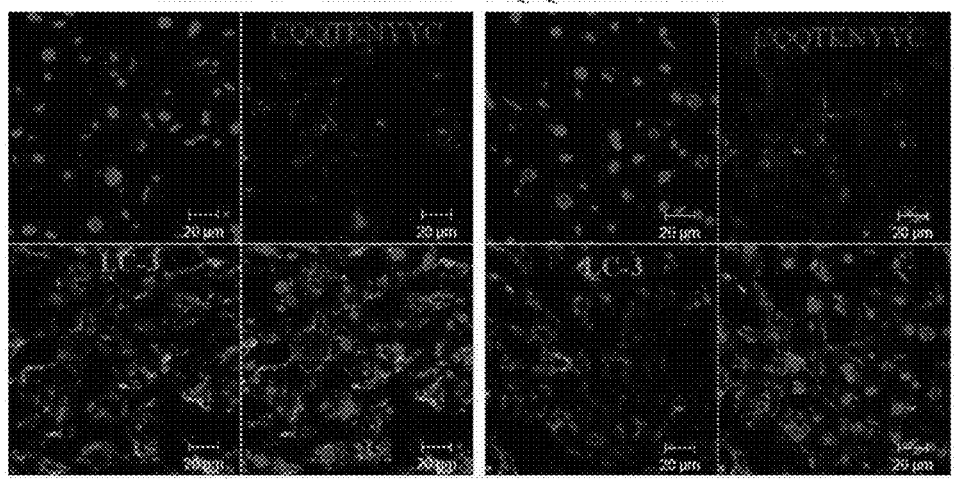
tumor : FPR675-CNSSSVDKC
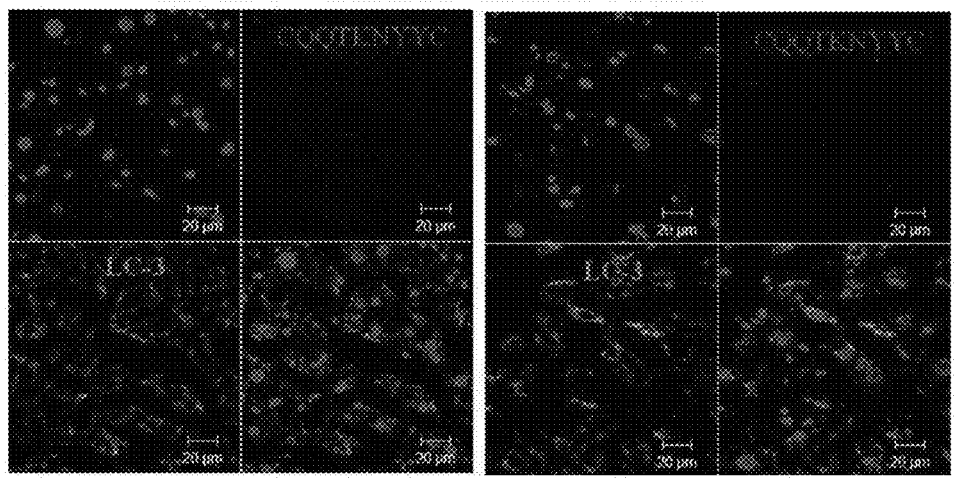

PEPTIDE FOR TARGETING AUTOPHAGIC CELLS AND USE THEREOF

CROSS REFERENCE TO RELATED APPLICATIONS

This application is a continuation of PCT Application No. PCT/KR2016/001943, filed Feb. 26, 2016, which claims priority to and the benefit of Korean Patent Application No. 10-2015-0028567 filed on Feb. 27, 2015, the entire contents of each of which are incorporated herein by reference.

TECHNICAL FIELD

The present invention relates to peptides for targeting autophagic cells and their uses, and more particularly, to peptides having an amino acid sequence represented by the general formula (I) and specifically binding to an autophagic cell, and a composition for detecting autophagic cells comprising the same as an active ingredient, a composition for drug delivery comprising the same as an active ingredient, and a composition for imaging comprising the same as an active ingredient, and the like.

BACKGROUND ART

Autophagy, apoptosis and necrosis are key players in cell death and play an important role in many human diseases. Strategies to regulate relevant pathways have been successfully applied to the treatment of a variety of diseases [Kepp, O., et al., Nat Rev Drug Discov, 2011.10 (3): p. 221-37]. However, the relevance between autophagy and apoptosis has not been fully explained. This is due to the absence of highly accurate tools or methods that can specifically distinguish intracellular phenomena that are complexly inter-related.

Various methods have been used to measure autophagy at cellular and biological levels. Specifically, the conversion of LC3 (LC3 conversion), LC3-II puncta formation and measurement of autophagic flux are currently widely used methods for autophagy detection.

The measurement of LC3 conversion detects the conversion of LC3-I to LC3-II using immunoblotting, and LC3-II itself has a problem that it is difficult to quantify the relative amount due to decomposition by self-digestion. And the sensitivity of the LC3-II antibody is much higher than that of LC3-I, making it impossible to compare the relative amounts between the two.

The LC3-II puncta formation is measured by artificially expressing the GFP-LC3 fusion protein by transfection into cells to observe the fluorescence dot shape observed when the autophagosome is formed. This method has a disadvantage in that it is difficult to distinguish the autophagic activated cell from the normal cell because a considerable part of the dot shape is observed in the normal cells as well as the cells in which the self-digestion occurs. In addition, there are disadvantages in that overexpression of GFP-LC3 protein expressed in the cells generates fluorescence points in normal cells regardless of autophagy and GFP-LC3 protein expression itself induces self-digestion (Mizushima N. et al., Cell 2010, 140, 313-326.). Moreover, the labeling ability of GFP-LC3 protein is remarkably decreased in autolysosome produced after fusion with lysosome.

There is a method of measuring autophagic flux by treating cells with chloroquine or the like which is a lysosomal inhibitor. However, the chloroquine has been shown to induce cell death caused by apoptosis in the cells to be tested (Chuandong Fan et al., Bioorganic & amp; Medicinal Chemistry, 2006, Volume 14, Issue 9, pp. 3218-3222).

In addition, monodanysylcadaverine (MDC), a fluorescent dye, is widely used in the staining of autophagic vacuoles, but its specificity remains unclear. More importantly, most of the methods described above are used to measure autophagy only in vitro or ex vivo imaging.

In vivo imaging of autophagy has been gained to some extent by methods using transgenic mice that are presently systemically expressing LC3 fused mainly with GFP (Tian, F F, et al., 2010; Mizushima, N., et al., 2004). Another method is to inject MDC and chloroquine to measure autophagic flux in the myocardium. However, there is no complete method for monitoring autophagy in vivo (Mizushima, N., et al., 2010).

Thus, there is a need in the art for universal molecular probes that can be used both in vitro and in vivo as well as accessible and permeable to a variety of tissues in molecular imaging of autophagy.

PRIOR ART LITERATURE

Non-Patent Document (Non-Patent Document 1) [1] Kepp, O., et al., Cell death has for drug discovery. Nat Rev Drug Discov, 2011.10 (3): p. 221-37.

(Non-Patent Document 2) [2] Mizushima, N., T. Yoshimori, and B. Levine, Methods in mammalian autophagy research. Cell, 2010.140 (3): p. 313-26.

(Non-Patent Document 3) [3] Tian, F F, et al., In vivo imaging of autophagy in a mouse stroke model. Autophagy, 2010.6 (8): p. 1107-1114.

(Non-Patent Document 4) [4] Mizushima, N., et al., In vivo analysis of autophagy in response to nutrient starvation using transgenic mice expressing a fluorescent autophagosome marker. Molecular Biology of the Cell, 2004. 15 (3): p. 1101-1111.

(Non-Patent Document 5) [5] Acharya, B., et al., In vivo imaging of myocardial cell death using a peptide probe and assessment of long-term heart function. J Control Release, 2013.172 (1): p. 367-73.

(Non-Patent Document 6) [6] Nishida, K., et al., The Role of Autophagy in the Heart. Cell Death Differ, 2009.16 (1): p. 31-8.

(Non-Patent Document 7) [7] Matsui, Y., et al., Distinct roles of autophagy in the heart during ischemia and reperfusion: roles of AMP-activated protein kinase and Beclin1 in mediating autophagy. CircRes, 2007.100 (6): p. 914-22.

(Non-Patent Document 8) [8] Jimenez, R E, D A Kubli, and A B Gustafsson, Autophagy and mitophagy in the myocardium: therapeutic potential and concerns. Br J Pharmacol, 2014, 171 (8): p. 1907-16

(Non-Patent Document 9) [9] Sciarretta, S., et al., Is autophagy in response to ischemia and reperfusion protective or detrimental for the heart? Pediatr Cardiol, 2011.32 (3): p. 275-81.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 7A and 7B are each a single cell image showing that the peptide of the present invention is bound to the cell membrane in autophagy-induced MDA-MB-231 cells (RB: rhodamine B labeled). SEQ ID NO: 1 and SEQ ID NO: 2 are respectively listed on each panel.

FIG. 10 shows LC3 antibody staining, one of the autophagy markers, and fluorescence-labeled peptides observed under a fluorescence microscope. Upper panel, CQQTKNYYC (SEQ ID NO: 2); lower panel, CNSSSVDKC (SEQ ID NO: 10).

DETAILED DESCRIPTION OF THE INVENTION

Technical Problem

Figure 1:
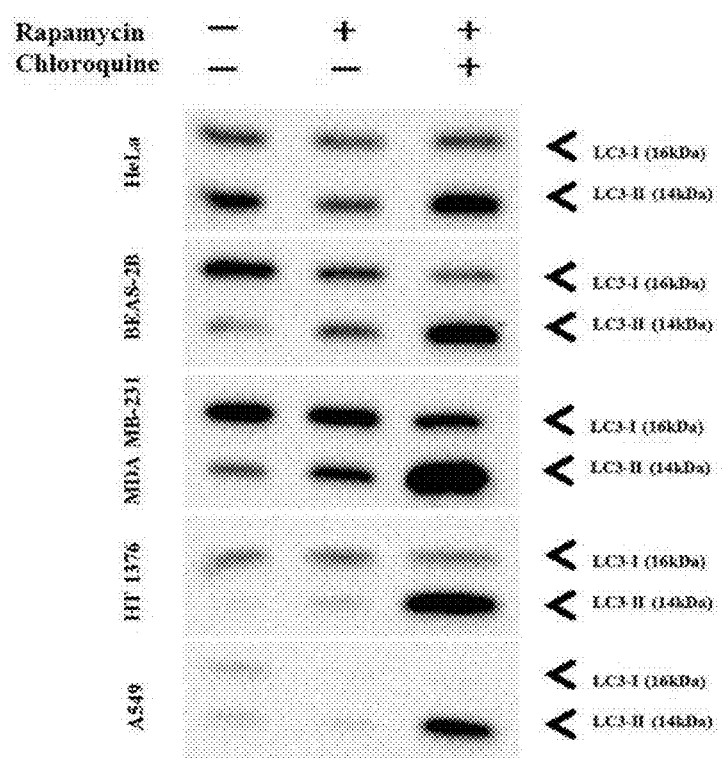
FIG. 1 shows the basic autophagy level and autophagy level induced by rapamycin alone and together with and chloroquine, a lysosomal inhibitor, against several cell lines of A549, HT1376, MDA-MB-231, BEAS-2B and HeLa, by western blotting of LC3 I and LC3 II proteins.

Accordingly, the inventors of the present invention have identified peptides that specifically bind to the cell membrane of autophagic cells, while searching for a highly sensitive probe which is capable of specifically targeting autophagic cells on various tissues, and can be non-invasively applied in vivo as well as in vitro (and ex vivo). The present invention found that the peptides were highly effective for detecting and imaging autophagy in vitro and in vivo, thereby completing the present invention.

Accordingly, an aspect of the present invention is to provide a polypeptide which specifically binds to an autophagic cell comprising the amino acid sequence represented by the following general formula (I), and its use;

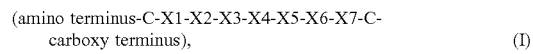

(amino terminus-C-X1-X2-X3-X4-X5-X6-X7-C-carboxy terminus), (I)

wherein C is cysteine,
X1 is any amino acid selected from the group consisting of lysine, glutamine, asparagine and proline; X2 is any amino acid selected from the group consisting of histidine, glutamine, threonine, and proline; X3 is any amino acid selected from the group consisting of histidine, threonine, glycine and asparagine; X4 is any amino acid selected from the group consisting of leucine, lysine, serine, and threonine; X5 is any amino acid selected from the group consisting of glycine, asparagine, proline, and aspartic acid; X6 is any amino acid selected from the group consisting of alanine, tyrosine and arginine; X7 is any amino acid selected from the group consisting of isoleucine, tyrosine, glutamic acid and serine.

Another aspect of the present invention is to provide a method for preventing or treating myocardial infarction, comprising administering to a subject in need thereof an effective amount of the polypeptide and a therapeutic agent for myocardial infarction attached thereto.

Still another aspect of the present invention is to provide a method for treating a neoplastic disease, comprising administering to a subject in need thereof an effective amount of polypeptide and an anti-neoplastic disease agent attached to the polypeptide.

Still further another aspect of the present invention is to provide a method for preventing or treating a stroke, comprising administering to a subject in need thereof an effective amount of polypeptide and a therapeutic agent for stroke attached to the polypeptide.

Technical Solution

An embodiment of the present invention provides a polypeptide which specifically binds to an autophagic cell comprising the amino acid sequence represented by the following general formula (I):

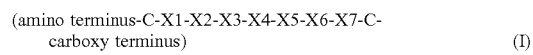

(amino terminus-C-X1-X2-X3-X4-X5-X6-X7-C-carboxy terminus) (I)

wherein C is cysteine,
X1 is any amino acid selected from the group consisting of lysine, glutamine, asparagine and proline; X2 is any amino acid selected from the group consisting of histidine, glutamine, threonine, and proline; X3 is any amino acid selected from the group consisting of histidine, threonine, glycine and asparagine; X4 is any amino acid selected from the group consisting of leucine, lysine, serine, and threonine; X5 is any amino acid selected from the group consisting of glycine, asparagine, proline, and aspartic acid; X6 is any amino acid selected from the group consisting of alanine, tyrosine and arginine; X7 is any amino acid selected from the group consisting of isoleucine, tyrosine, glutamic acid and serine.

Another embodiment of the present invention provides a polynucleotide comprising a nucleotide sequence encoding the polypeptide.

Another embodiment of the present invention provides a vector comprising the polynucleotide.

Another embodiment of the present invention provides a transformant transformed with the vector.

Another embodiment of the present invention provides a composition for detecting autophagic cells comprising the polypeptide as an active ingredient.

Another embodiment of the present invention provides a method for detecting autophagic cells comprising: (a) mixing the polypeptide with a sample; (b) removing said unpaired or non-specifically bound polypeptide; and (c) determining the binding of the polypeptide to the autophagic cells and the location of the autophagic cells.

Another embodiment of the present invention provides a composition for autophagic cell-specific drug delivery comprising the polypeptide as an active ingredient.

Another embodiment of the present invention provides a composition for autophagy imaging comprising the polypeptide as an active ingredient.

Another embodiment of the present invention provides a pharmaceutical composition for preventing and treating myocardial infarction comprising the polypeptide and a therapeutic agent for myocardial infarction attached thereto as an active ingredient.

Another embodiment of the present invention provides a composition for imaging myocardial infarction site comprising the polypeptide as an active ingredient.

Another embodiment of the present invention provides a pharmaceutical composition for preventing and treating a neoplastic disease comprising the polypeptide and an anti-neoplastic agent attached thereto as an active ingredient.

Another embodiment of the present invention provides a composition for imaging a neoplastic disease site comprising the polypeptide as an active ingredient.

Another embodiment of the present invention provides a pharmaceutical composition for preventing and treating stroke, comprising the polypeptide and a therapeutic agent for stroke attached thereto as an active ingredient.

Another embodiment of the present invention provides a composition for imaging a stroke site comprising the polypeptide as an active ingredient.

Another embodiment of the present invention provides a method for preventing or treating myocardial infarction, comprising administering to a subject in need thereof an effective amount of the polypeptide and a therapeutic agent for myocardial infarction attached thereto.

Another embodiment of the present invention provides a method for treating a neoplastic disease, comprising administering to a subject in need thereof an effective amount of polypeptide and an anti-neoplastic agent attached to the polypeptide.

Another embodiment of the present invention provides a method for preventing or treating stroke, comprising administering to a subject in need thereof an effective amount of polypeptide and a therapeutic agent for stroke attached to the polypeptide.

Hereinafter, the present invention will be described in detail.

As used herein, the term "polypeptide" is used interchangeably with "protein" or "peptide" and refers to a polymer of amino acid residues as commonly found in natural state proteins.

As used herein, the term "polynucleotide" or "nucleic acid" refers to a deoxyribonucleotide or ribonucleotide in a single- or double-stranded form. Unless otherwise limited, it also includes known analogs of natural nucleotides that hybridize to nucleic acids in a manner similar to naturally occurring nucleotides.

As used herein, the term "expression" refers to the production of a protein or nucleic acid in a cell.

As used herein, the one letter (three letters) of amino acids refer to the following amino acids according to standard abbreviations in the biochemistry:

A (Ala): alanine; C (Cys): cysteine; D (Asp): aspartic acid; E (Glu): glutamic acid; F (Phe): phenylalanine; G (Gly): glycine; H (His): histidine; I (Ile): isoleucine; K (Lys): lysine; L (Leu): leucine; M (Met): methionine; N (Asn): Asparagine; O (Ply) pyrrolic acid; P (Pro): proline; Q (Gln): Glutamine; R (Arg): arginine; S (Ser): serine; T (Thr): threonine; U (Sec): selenocysteine, V (Val): valine; W (Trp): tryptophan; Y (Tyr): Tyrosine.

In this specification, the term "autophagy" is used interchangeably with "self-predation (self-feeding)", "self-digestion (self-digestion)", etc., and means a life phenomenon that recycles damaged organelles or proteins, which have been functionally expired, by using lysosomal degradation process in cells. Specifically, in the early stages of autophagy, the cytoplasm and intracellular organelles degenerate into an autophagosome of a double-membrane-associated structure. The autophagosome then fuses with the lysosome to form an autolysosome, which is degraded and reused by lysosomal hydrolase.

As used herein, the term "autophagic cell" refers to a cell in which the autophagy phenomenon occurs or is progressing.

The polypeptide of the present invention is represented by the following sequence formula (I) and is characterized in that it specifically binds to autophagic cells;

(amino terminus-C-X1-X2-X3-X4-X5-X6-X7-C-carboxy terminus)     (I)

provided that C is cysteine,

X1 is any amino acid selected from the group consisting of lysine, glutamine, asparagine and proline; X2 is any amino acid selected from the group consisting of histidine, glutamine, threonine, and proline; X3 is any amino acid selected from the group consisting of histidine, threonine, glycine and asparagine; X4 is any amino acid selected from the group consisting of leucine, lysine, serine, and threonine; X5 is any amino acid selected from the group consisting of glycine, asparagine, proline, and aspartic acid; X6 is any amino acid selected from the group consisting of alanine, tyrosine and arginine; X7 is any amino acid selected from the group consisting of isoleucine, tyrosine, glutamic acid and serine.

Preferably, the polypeptide of the present invention for the above-mentioned sequence formula (I) is that wherein X1 is lysine or glutamine; X2 is histidine or glutamine; X3 is histidine or threonine; X4 is leucine or lysine; X5 is glycine or asparagine; X6 is alanine or tyrosine; And X7 is isoleucine or tyrosine.

More preferably, the polypeptide of the present invention may be a polypeptide comprising an amino acid sequence selected from the group consisting of SEQ ID NO: 1 to SEQ ID NO: 4.

As described above, the polypeptide of the present invention, which is composed of a specific combination of amino acid sequences, specifically targets autophagic cells and binds to the cell membrane of autophagic cells. The autophagic cell-specific polypeptides of the present invention can be applied to a variety of tissues and cells in vitro and in vivo compared to various molecular means previously used for intracellular autophagy measurement and detection. And the polypeptide of the present invention not only provides accurate information on the autophagy phenomenon, but also can detect intracellular autophagy in its early stage. In particular, the early detection and diagnosis of autophagy in cells is a means for predicting the fate of cells in the tissue. If the autophagy phenomenon persists for a long period of time in the cells, the cells die without being able to tolerate autophagy. Therefore, early detection (or diagnosis) of autophagy is very important for diagnosis and research of autophagy-related diseases.

The effects of such a polypeptide of the present invention are well illustrated in the examples of the present specification.

In one example of the present invention, screening of the M13 phage library revealed four peptides, which specifically bind to autophagic cells, CKHHLGAIC (AtgPep-1, SEQ ID NO: 1), CQQTKNYYC (AtgPep-2, SEQ ID NO: 2), CNTGSPYEC (AtgPep-3, SEQ ID NO: 3) and CPPNTDRSC (AtgPep-4, SEQ ID NO: 4) (see Example 1) and confirmed the binding specificity of the peptides to autophagic cells (see Example 2). As a result, the peptides of the present invention did not bind to apoptosis-inducing cells while specifically binding to autophagic cells at the early stage of autophagy induction in the cell, thereby being able to detect autophagy thereof.

In addition, it was confirmed that the peptide of the present invention was capable of autophagy-specific targeting and binding not only in vitro but also in animal models. As a result, in the biomedical image, it was confirmed that the peptide of the present invention was targeted to the tumor at a significantly higher level after induction of autophagy. Similarly, in the tissue, the target signal of the peptide of the present invention was higher than that of the control group (See Example 2).

The polypeptide of the present invention may be derived from nature, and may be synthesized using a known polypeptide synthesis method (genetic engineering method, chemical synthesis). Genetic engineering methods construct nucleic acids (e.g., polynucleotides of SEQ ID NO: 5 to SEQ ID NO: 8) that encode the polypeptide or functional equivalents thereof, for example, according to conventional methods. The nucleic acid can be constructed by PCR amplification using an appropriate primer. Alternatively, DNA sequences may be synthesized by standard methods known in the art, for example, using an automated DNA synthesizer (commercially available from Biosearch or Applied Biosystems). The constructed nucleic acid is inserted into a vector comprising one or more expression control sequences (e.g., promoters, enhancers, etc.) to regulate operatively for the expression of the nucleic acid. Then, the host cell is transformed with a recombinant expression vector. The resulting transformant is cultured under the suitable conditions for expression of the nucleic acid, and the substantially pure polypeptide expressed by the nucleic acid is recovered from the culture. The recovery can be carried out using methods known in the art (for example, chromatography). As used herein, the term "substantially pure polypeptide" means that the polypeptide according to the present invention is substantially free of any other protein derived from the host cell. Genetic engineering methods for the synthesis of polypeptides of the present invention can be found in the following references: Maniatis et al., Molecular Cloning; A laboratory Manual, Cold Spring Harbor Laboratory, 1982; Sambrook et al., Molecular Cloning: A Laboratory Manual, Cold Spring Harbor Press, NY, Second (1998) and Third (2000) Editions; Gene Expression Technology, Method in Enzymology, Genetics and Molecular Biology, Method in Enzymology, Guthrie & Fink (eds.), Academic Press, San Diego, Calif., 1991; And Hitzeman et al., J. Biol. Chem., 255: 12073-12080, 1990.

In addition, the polypeptide of the present invention can be easily prepared by chemical synthesis (Creighton, Proteins, Structures and Molecular Principles, WH Freeman and Co., NY, 1983) known in the art. Representative methods include, but are not limited to, liquid or solid phase synthesis, fractional condensation, F-MOC or T-BOC chemistry (Chemical Approaches to the Synthesis of Peptides and Proteins, Williams et al., Boca Raton Fla., 1997; A Practical Approach, Athert on & Sheppard, Eds., IRL Press, Oxford, England, 1989).

In addition, the polypeptide of the present invention includes not only polypeptides having the amino acid sequences described above but also polypeptides having the amino acid sequence variants thereof, within the scope of the present invention. Polypeptide variants of the present invention means polypeptides having one or more amino acid residues in the amino acid sequence of the present invention which have different sequences by deletion, insertion, non-conservative or conservative substitution, substitution of amino acid analog, or a combination thereof. Amino acid exchanges that do not overall alter the activity of the molecule are known in the art (H. Neurath, R L Hill, The Proteins, Academic Press, New York, 1979).

In some cases, the polypeptide of the present invention may be modified by phosphorylation, sulfation, acrylation, glycosylation, methylation, farnesylation, and the like.

The present invention provides a polynucleotide comprising a nucleotide sequence encoding said polypeptide.

The polynucleotide is not particularly limited in its base combination constituting the polynucleotide so long as it can encode the polypeptide of the present invention. The polynucleotide may be provided as a nucleic acid molecule in the form of a single chain or double chain including DNA, cDNA, and RNA sequences.

Preferably, the polynucleotide of the present invention may be a polynucleotide encoding any one of the polypeptides selected from the group consisting of SEQ ID NO: 1 to SEQ ID NO: 4. For example, the polynucleotide may be any one selected from the group consisting of SEQ ID NO: 5 to SEQ ID NO: 8 Sequence. Specifically, the polynucleotide encoding the polypeptide of SEQ ID NO: 1 may be the nucleotide sequence of SEQ ID NO: 5, while the polynucleotide encoding the polypeptide of SEQ ID NO: 2 may be the nucleotide sequence of SEQ ID NO: 6. The polynucleotide encoding the polypeptide of SEQ ID NO: 3 may be the nucleotide sequence of SEQ ID NO: 7, while the polynucleotide encoding the polypeptide of SEQ ID NO: 4 may be the one having the nucleotide sequence of SEQ ID NO: 8, but are not limited thereto. SEQ ID NO: 5, tgtaagcatc atctgggtgc gatttgc; SEQ ID NO: 6, tgtcagcaga cgaagaatta ttattgc; SEQ ID NO: 7, tgtaatactg gttcgcctta tgagtgc; SEQ ID NO: 8, tgtccgccga atactgatcg ttcgtgc.

The present invention provides a vector comprising the polynucleotide.

The vector of the present invention includes, but is not limited to, a plasmid vector, a cosmid vector, a bacteriophage vector, and a viral vector. The vector of the present invention may be a conventional cloning vector or an expression vector. The expression vector may contain an expression control sequence such as a promoter, an operator, an initiation codon, a stop codon, a polyadenylation signal, and an enhancer as well as a signal sequence or a leader sequence, and can be produced variously according to its purpose. The polynucleotide sequence according to the present invention may be operably linked to an expression control sequence. The operably linked gene sequence and expression control sequence may be contained within an expression vector containing a selection marker and a replication origin. The term "Operably linked" means that gene expression is possible when appropriate molecules are attached to expression control sequences and that one nucleic acid fragment is associated with another nucleic acid fragment and its function or expression is influenced by other nucleic acid fragments. The term "Expression control sequence" means a DNA sequence that regulates the expression of a polynucleotide sequence operably linked to a particular host cell. Such regulatory sequences include promoters for conducting transcription, any operator sequences for regulating transcription, sequences encoding mRNA ribosome binding sites, and sequences controlling the termination of transcription and translation. The vector also includes a selection marker for selecting a host cell containing the vector, and a replication origin if the vector is a replicable vector.

The present invention provides a transformant transformed with said vector.

Transformation with these vectors can be carried out by transformation techniques known to those skilled in the art. Preferably, microprojectile bombardment, electroporation, calcium phosphate ($CaPO_4$) precipitation, calcium chloride ($CaCl_2$) precipitation, PEG-mediated fusion, microinjection, and a liposome-mediated method can be used.

The term "transformant" may be used interchangeably with "host cell" and means a prokaryotic or eukaryotic cell comprising a heterologous DNA introduced into the cell by any means (e.g., electrophoresis, calcium phosphatase precipitation, microinjection, transformation, virus infection, etc.).

In the present invention, the transformant can be used for all kinds of single cell organisms commonly used in the field of cloning such as prokaryotic microorganisms including various bacteria (for example, Clostridia genus, *E. coli*, etc.), eukaryotic microorganisms such as yeast, and cells derived from higher eukaryotes, including insect cells, plant cells, mammals and the like, but the present invention is not limited thereto. Since the expression amount and modification of the protein are different depending on a host cell, a host cell most suitable for a desired purpose of a person skilled in the art can be selected and used. For example, the microorganism used as a transformant in the present invention is *Escherichia coli, Bacillus subtilis; Streptomyces* spp., *Pseudomonas* spp. microorganisms, *Proteus mirabilis, Staphylococcus* spp., *Agrobacterium tumefaciens*, but is not limited thereto.

The present invention provides a composition for detecting autophagic cells comprising the polypeptide as an active ingredient. Preferably, the present invention provides a composition for detecting autophagic cells comprising a polypeptide consisting of any one of the amino acid sequences selected from the group consisting of SEQ ID NO: 1 to SEQ ID NO: 4 as an active ingredient.

In order to facilitate identification, detection and quantification of the binding of the polypeptide of the present invention to autophagic cells, the polypeptide of the present invention may be provided in a labeled state. That is, they may be provided as links (e.g., covalently bonded or bridged) to detectable labels. The detectable label is a chromogenic enzyme (e.g., peroxidase, alkaline phosphatase), radioactive isotopes (such as $^{18}F$, $^{123}I$, $^{124}I$, $^{125}I$, $^{32}P$, $^{35}S$, $^{67}Ga$), chromophore, a luminescent material or a fluorescent material (such as FITC, RITC, GFP (Green Fluorescent Protein), EGFP (Enhanced Green Fluorescent Protein), RFP (Red Fluorescent Protein), DsRed (Discosoma sp. red fluorescent protein), Cyan Fluorescent Protein (CFP), Cyan Green Fluorescent Protein (CGFP), Yellow Fluorescent Protein (YFP), Cy3, Cy5 and Cy7.5), magnetic resonance imaging materials (such as Gadolinium (Gd), superparamagnetic particles and ultrasmall superparamagnetic particles).

While a labeling-based detection method is well known in the art, for example, it may be carried out by the method described below. If a fluorescent substance is used as a detectable label, immunofluorescence staining may be carried out. For example, the peptides of the present invention labeled with a fluorescent substance can be reacted with a sample, and unbound or nonspecific binding products can be removed, and fluorescence by the peptide can be observed under a fluorescence microscope. In the case of using an enzyme as a detectable label, the absorbance can be measured by the color reaction of the substrate through an enzyme reaction, while in the case of a radioactive substance, the amount of emitted radiation can be measured. The detection result can also be imaged in accordance with a known imaging method according to the type of the detection label.

The present invention provides a method for detecting autophagic cells comprising the steps of: (a) mixing with said polypeptide a sample; (b) removing unpaired or nonspecifically bound polypeptide; and (c) determining the binding of the polypeptide to the autophagic cells and the location of the autophagic cells. At this time, the detection method of the peptide is carried out in order to check the binding status and the location. The detection method of the peptide can be carried out according to the method described above or according to a known method.

In the present invention, the term "sample" refers to a biological sample, including blood and other liquid samples of biologic origin, biopsy specimens, solid tissue samples such as tissue culture, or cells derived therefrom. The sample may be of animal, preferably can be obtained from a mammal. The sample can be pretreated prior to use with the detection. For example, the pretreatment may include an extraction, concentration, inactivation of interfering components, addition of reagents, and the like.

Further, since the polypeptide of the present invention possesses therefore superior effects of binding to autophagic cells specifically, it can be used as an intelligent drug delivery vehicle that selectively delivers a drug to the autophagic cell (ultimately in vivo to a diseased site where the autophagic cell is present). Thus the present invention provides a composition for the autophagic cell-specific drug delivery, comprising the polypeptide as an active ingredient.

The drug delivery composition of the present invention is capable of specifically delivering a drug to the affected part of an autophagy-related disease accompanied by a pathological autophagy phenomenon, and the autophagy-related diseases are not particularly limited as long as they are autophagy-related diseases known in the art. For example, degenerative neurological diseases, stroke, neoplastic diseases, cardiomyopathy, myocardial infarction, aging, type II PCD (programmed cell death), type 2 diabetes, and bacterial infections.

Specifically, the degenerative neurological diseases include, for example, dementia, Parkinson's disease, Alzheimer's disease, Huntington's disease, Pick's Disease and Parkinson-ALS (amyotrophic lateral sclerosis)-dementia complex and the like, but is not limited thereto.

In addition, the above-mentioned neoplastic diseases are diseases that have pathological symptoms due to malignant tumors, such as lung cancer, liver cancer, colon cancer, pancreatic cancer, stomach cancer, breast cancer, ovarian cancer, renal cancer, thyroid cancer, parathyroid cancer, esophageal cancer, prostate cancer, brain cancer, skin cancer, osteosarcoma, soft tissue sarcoma, glioma, lymphoma, nasopharyngeal cancer, throat cancer, adrenal cancer, colon cancer, ureter cancer, gallbladder cancer, bladder cancer, testicular cancer, cervical cancer, endometrial cancer, choriocarcinoma, head and neck cancer, malignant melanoma, leukemia, multiple myeloma, chronic myelogenous leukemia, aplastic anemia and the like.

More specifically, when the polypeptide of the present invention contained in the drug delivery composition is used in combination with a drug, agent such as a conventional anti-neoplastic agent, a stroke therapeutic agent, and a therapeutic agent for myocardial infarction, the agent is selectively delivered only to a diseased part (affected part) such as a neoplastic cell, a stroke site, and a myocardial infarction area due to the polypeptide of the present invention. Therefore, it is possible to increase the efficacy of the drug and at the same time to significantly reduce the adverse effects on normal tissues.

Thus, the present invention provides a pharmaceutical composition for preventing and treating a neoplastic disease comprising the polypeptide of the present invention and an anti-neoplastic agent combined therewith as an active ingredient; a pharmaceutical composition for preventing and treating myocardial infarction comprising the polypeptide of the present invention and a therapeutic agent for myocardial infarction attached thereto as an active ingredient, and a pharmaceutical composition for preventing and treating stroke comprising the polypeptide of the present invention and a therapeutic agent for stroke attached thereto as an active ingredient.

The anti-neoplastic agent that can be linked to the polypeptide of the present invention is not particularly limited as long as it is a known tumor therapeutic agent. For example, it may include at least one selected form the group consisting of paclitaxel, doxorubicin, vincristine, daunorubicin, vinblastine, actinomycin-D, docetaxel, etoposide, teniposide, bisantrene, homoharringtonine, Gleevec (STI-571), cisplatin, 5-fluouracil, adriamycin, methotrexate, busulfan, chlorambucil, cyclophosphamide, melphalan, nitrogen mustard, nitrosourea, streptokinase, urokinase, alteplase, angiotensin II inhibitor, aldosterone receptor inhibitor, erythropoietin, NMDA (N-methyl-D-aspartate) receptor inhibitors, lovastatin, rapamycin, celebrex, ticlopin, marimastat and trocade and the like.

In addition, the therapeutic agent for stroke and myocardial infarction can be used without limitation as long as they are conventionally used for the treatment of these diseases. For example, it includes drugs such as streptokinase, urokinase, and alteplase, which are thrombolytic drugs used to remove blood clots blocking blood vessels in stroke and myocardial infarction diseases. Also, it includes cardiac cytoprotective agents such as angiotensin II inhibitors, aldosterone receptor inhibitors and erythropoietin etc. In addition, it includes a brain cell protecting agent such as NMDA (N-methyl-d-aspartate) receptor inhibitor.

The binding between the above agents and the peptide of the present invention can be carried out by methods known in the art, for example, through covalent bonding, crosslinking, and the like. For this purpose, if necessary, the polypeptide of the present invention can be chemically modified to such an extent that its activity is not lost. The amount of the polypeptide of the present invention contained in the composition of the present invention may vary depending on the kind and amount of the therapeutic agent to be bound.

In the pharmaceutical composition of the present invention, the polypeptide of the present invention may be provided in a labeled state to facilitate identification, detection and quantification of binding to a target organ, as described above.

On the other hand, the pharmaceutical compositions according to the invention can be provided in a pure form of the peptide or a suitable form together with a pharmaceutically acceptable carrier. "Pharmaceutically acceptable" is physiologically acceptable and, when administered to humans, and typically refers to a non-toxic composition that does not cause such allergic reactions or similar reactions as gastrointestinal disorder and dizziness. Such carriers include all kinds of solvents, dispersion media, oil-in-water or water-in-oil emulsions, aqueous compositions, liposomes, microbeads and microsomes, biodegradable nanoparticles and the like.

On the other hand, the pharmaceutical compositions according to the present invention can be formulated with a suitable carrier depending on the administration route. The route of administration of pharmaceutical compositions according to the present invention may be administered orally or parenterally, but are not limited to. Non-oral routes of administration, for example, include various routes such as the transdermal, intranasal, intraperitoneal, intramuscular, subcutaneous or intravenous.

When the pharmaceutical composition of the present invention is orally administered, the pharmaceutical composition of the present invention may be formulated in the form of powders, granules, tablets, pills, sugar tablets, capsules, solutions, gels, syrups, suspensions, wafers or the like according to methods known in the art, together with a suitable oral administration carrier. Examples of suitable carriers include saccharides including lactose, dextrose, sucrose, sorbitol, mannitol, xylitol, erythritol and maltitol, and starches including corn starch, wheat starch, rice starch and potato starch, cellulose such as methyl cellulose, sodium carboxymethyl cellulose and hydroxypropylmethyl-cellulose and the like, fillers such as gelatin, polyvinylpyrrolidone and the like. In addition, crosslinked polyvinylpyrrolidone, agar, alginic acid or sodium alginate may optionally be added as a disintegrant. Furthermore, the cross-linked polyvinyl pyrrolidone, agar, alginic acid or sodium alginate, etc. as the case may be, it may be added as disintegrating agents. Furthermore, the pharmaceutical composition may further comprise an anti-coagulant, lubricants, wetting agents, perfumes, emulsifying agents and preservatives.

When the pharmaceutical composition of the present invention is parenterally administered, the pharmaceutical composition of the present invention can be formulated according to methods known in the art in the form of an injections, transdermal drug delivery, and nasal inhalation together with a suitable carrier for parenteral use. In the case of the injections, they must be sterilized and protected from contamination of microorganisms such as bacteria and fungi. Examples of suitable carriers for injectables include, but are not limited to, water, ethanol, polyol (e.g., glycerol, propylene glycol and liquid polyethylene glycol, and the like), mixtures thereof and/or a solvent or dispersion medium containing vegetable oil. More preferably, suitable carriers include, but are not limited to, Hank's solution, Ringer's solution, phosphate buffered saline (PBS) containing triethanolamine or isotonic solutions such as sterile water for injection, 10% ethanol, 40% propylene glycol and 5% dextrose etc. To protect the injection from microbial contamination, it may further comprise various antibacterial and antifungal agents such as paraben, chlorobutanol, phenol, sorbic acid, thimerosal. In addition, the injection may further comprise an isotonic agent such as sugar or sodium chloride in most cases. These formulations are described in the literature, which is a prescription commonly known in pharmaceutical chemistry (Remington's Pharmaceutical Science, 15th Edition, 1975, Mack Publishing Company, Easton, Pa.).

In the case of inhalation dosage forms, the compounds used according to the present invention may be formulated in a pressurized pack or a pressurized pack using a suitable propellant, for example dichlorofluoromethane, trichlorofluoromethane, dichlorotetrafluoroethane, carbon dioxide or other suitable gases. It can be conveniently delivered in the form of an aerosol spray from a nebulizer. In the case of a pressurized aerosol, the dosage unit may be determined by providing a valve to deliver a metered amount. For example, gelatin capsules and cartridges for use in an inhaler or insufflator may be formulated to contain a powder mix of the compound and a suitable powder base such as lactose or starch.

There can be others with the reference to that in a pharmaceutical acceptable carrier are described in the following literature (Remington's Pharmaceutical Sciences, 19th ed., Mack Publishing Company, Easton, Pa., 1995).

In addition, the pharmaceutical composition according to the present invention may further comprise one or more buffering agents (e.g., saline or PBS), carbohydrate (e.g., glucose, mannose, sucrose or dextran), a stabilizer (sodium bisulfite, sodium sulfite, or ascorbic acid), antioxidants, bacteriostatic agents, chelating agents (e.g., EDTA or glutathione), adjuvant (e.g., aluminum hydroxide), suspending agents, thickening agents and/or preservatives (benzalkonium chloride, methyl- or propyl-parabens and chlorobutanol).

In addition, the pharmaceutical compositions of the present invention may be formulated using methods known in the art so as to provide rapid, sustained or delayed release of the active ingredient after administration to the mammal.

A pharmaceutical composition formulated in the same manner as described above can be administered via various routes including oral, transdermal, subcutaneous, intravenous and intramuscular in an effective amount. The term "effective amount" as used herein refers to the amount of substance that enables the diagnosis or therapeutic effect to be tracked when administered to a patient. The dose of the pharmaceutical composition according to the present invention can be appropriately selected according to the administration route, administration target, the disease and its severity, age, sex, body weight, individual differences and disease condition. Preferably, the pharmaceutical composition comprising the peptide of the present invention may vary in the content of the active ingredient depending on the degree of the disease, and it may be usually administered on an adult basis several times a day with an effective dose of 1 mg to 1000 mg per administration.

Since the polypeptide of the present invention specifically binds to autophagic cells, it is possible to image a lesion in which autophagy is progressing in vivo (and ex-vivo) together with any labeling means (imaging means). Therefore, the present invention provides a composition for autophagy imaging comprising the polypeptide as an active ingredient.

As used herein, the autophagy imaging can be understood by those skilled in the art as imaging and diagnosis of autophagy-related disease, and the autophagy-related diseases are as described above. Specifically, for example, the composition for imaging of the present invention comprises a composition for imaging or diagnosis of a myocardial infarction site containing the polypeptide of the present invention as an active ingredient, a composition for imaging or diagnosing a neoplastic disease site containing the polypeptide of the present invention as an active ingredient; or a composition for imaging a stroke site including the polypeptide of the present invention as an active ingredient. However, the present invention is not limited thereto.

At this time, the imaging and diagnosis of the disease can include, but not limited to, the purpose of initial diagnosis of a disease, progress of treatment, progress of treatment, monitoring of response to a therapeutic agent, and the like. The peptide of the present invention may be provided in a labeled state to facilitate identification, detection and quantification of binding, as described above.

The present invention also provides a method for preventing or treating myocardial infarction, comprising administering to a subject in need thereof an effective amount of the polypeptide and a therapeutic agent for myocardial infarction attached thereto.

The present invention provides a method for treating a neoplastic disease, comprising administering to a subject in need thereof an effective amount of polypeptide and an anti-neoplastic agent attached to the polypeptide.

The present invention provides a method for preventing or treating stroke, comprising administering to a subject in need thereof an effective amount of polypeptide and a therapeutic agent for stroke attached to the polypeptide.

As described above, myocardial infarction, neoplastic disease and stroke of the present invention belong to autophagy-related diseases.

In addition, the therapeutic agent for myocardial infarction, the anti-neoplastic agent and the therapeutic agent for stroke according to the present invention can be used without limitation as long as they are used for the treatment of these diseases and this is as described above.

The term "effective amount" of the present invention refers to an amount that represents a therapeutic and preventive effect of the disease when administered to a patient. The subject may be an animal, preferably a mammal, particularly an animal, including a human, and may be an animal derived cell, tissue, organ, or the like. The subject may be a patient requiring treatment.

Advantageous Effects

The peptide of the present invention specifically binds to the cell membrane of autophagic cells, and is applicable to various kinds of tissues and cells. Also the peptide of the present invention is remarkably effective in detecting and imaging autophagy in vitro and in vivo.

Hereinafter, the present invention will be described in detail.

However, the following examples are illustrative of the present invention, and the contents of the present invention are not limited to the following examples.

Example 1

Identification of Peptides that Specifically Target Autophagy Cells
<1-1> Selection of Cell Lines for Phage Screening
Rapamycin 1 (provided by diluting in DMEM medium that does not contain FBS) or rapamycin (1) with chloroquine (20), lysosomal inhibitor, were treated for 4 hours in cell lines of A549, HT1376, MDA-MB-231, HeLa and BEAS-2B for inducing autophagy. After 4 hours, the cells were washed two times with 1×PBS, followed by a western blotting was carried out to investigate the protein levels of LC3 I and LC3 II (hereinafter referred to as, LC3 I/II). In order to perform the western blotting, the cells were first lysed with RIPA buffer with 1/ml protease inhibitor cocktail in the drug-treated cells. The whole cell extracts were fractionated by SDS-PAGE, and transferred to a nitrocellulose membrane using a dry blot (Bio-Rad). The membranes were incubated with TBST (10 mM Tris, pH 8.0, 150 mM NaCl, 0.5% Tween 20) containing 5% nonfat milk for 60 minutes, then washed once with TBST. The membrane was treated with rabbit antibody against human LC3 I/II (abcam) and stirred overnight at 4° C. The membrane was washed 3 times for 10 min with TBST, then was incubated for 1 hour with the HRP-labeled antibody (mouse anti-rabbit IgG-HRP, Santa Cruz, Inc.) against the rabbit antibody isolated from a mouse as a secondary antibody (1:3000 dilution). After washing three times with TBST and developing according to the protocol of the manufacturer of the ECL system (Amersham Biosciences), an image was detected with a luminescent image analyzer (LAS100 Plus, Fujifilm, Japan).

FIG. 1 shows the basic autophagy levels in the A549, HT1376, MDA-MB-231, HeLa and BEAS-2B cell lines; and autophagy levels induced by rapamycin in this experiment through increased production of LC3 II protein. The basic level of autophagy was different according to cell line. HT1376 and A549 cells showed low basal autophagy levels, while MDA-MB-231 and HeLa cells had a high level of autophagy. MDA-MB-231 and HeLa cells also showed higher autophagy induction than HT1376 and A549 cells when autophagy was induced by rapamycin. Therefore, MDA-MB-231 and HeLa cells were selected for the following studies. On the other hand, when chloroquine, which is a lysosomal inhibitor, was treated together with rapamycin, it was observed that the production of LC3 II protein was further increased in all the cells, verifying that the induction of the autophagy was not nonspecific due to lysosomal degradation, but specific to autophagy respectively.

<1-2> Bio-Panning of Phage Library—Direct Screening Method

Figure 2:
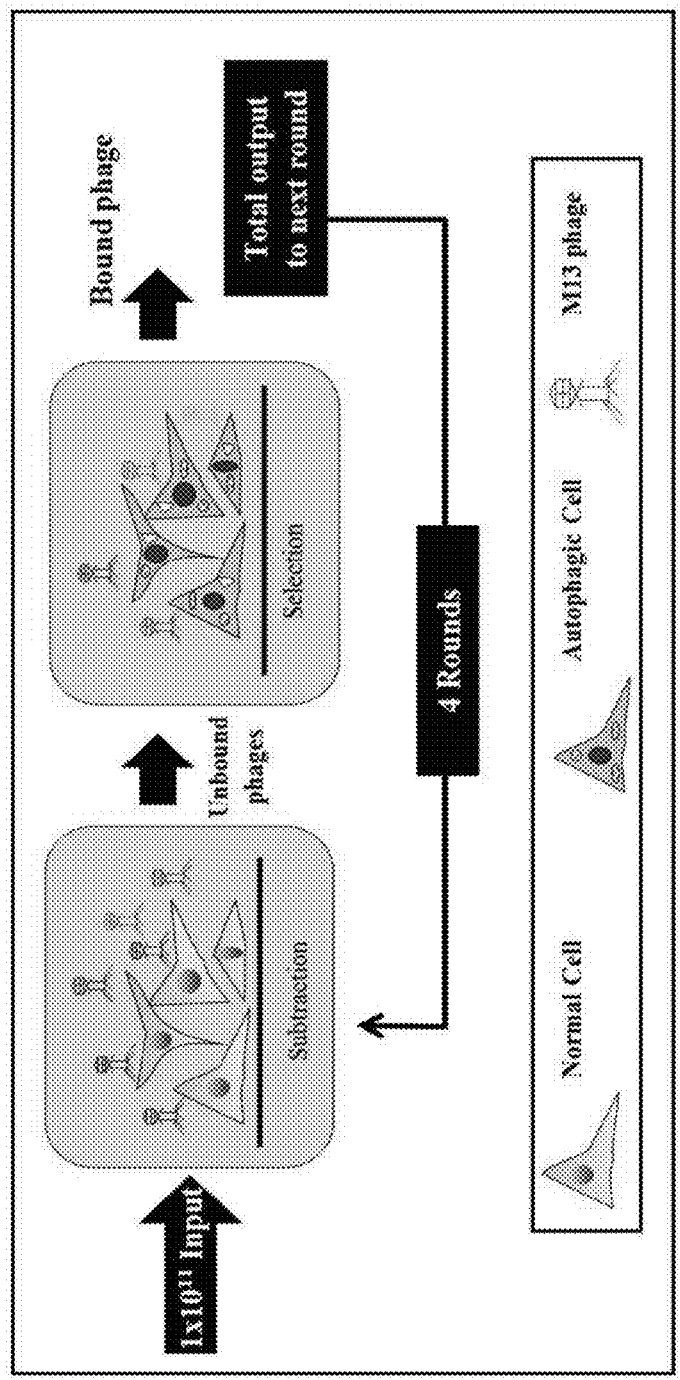
FIG. 2 is a schematic diagram showing the phage library screening strategies (direct bio-panning) used in the present invention.

The M13 phage library displaying the CX7C (C: cysteine, X: any amino acid) random peptide fused with the pIII protein was purchased from New England Biolabs (Ipswich, Mass.) and used for bio-panning. In the present invention, the schematic diagram of the bio-panning strategy is shown in FIG. 2. Detailed process is as follows. HeLa or MDA-MB-231 cells were plated on 35 mm culture dishes and reached a confluence of 70-80% the following day. The cells were treated with rapamycin (diluted in DMEM medium without FBS) for 4 hours. The phage library of $2 \times 10^{11}$ pfu (plaque-forming unit) was incubated with rapamycin-untreated HeLa/MDA-MB-231 cells for 1 hour at 4° C. (negative selection or subtraction procedure). The non-binding phage on these cells were recovered and gently agitated with rapamycin-treated HeLa or MDA-MB-231 cells and cultured at 4° C. for 1 hour. Uncoupled phage were then washed with DMEM containing 10 mg/ml BSA (bovine serum albumin). The phages bound to the cells were eluted by incubation with 0.2 mol/L glycine-HCl (pH 2.2) containing 1 mg/ml BSA for 10 min at room temperature. The eluate was immediately neutralized with 1 M Tris-HCl (pH 9.1). Ten of the eluates were used for titration and the remaining eluted phage clones were dissolved in 1 ml DMEM and cultured together with rapamycin-untreated cells as described above. This process was repeated four times in total. After serial dilutions of the eluates were inoculated into E. coli in LB medium containing IPTG (isopropyl β-D-1-thiogalactopyranoside), X-gal and tetracycline and incubated overnight at 37° C., the titer of the phage was determined by counting the number of colonies.

Figure 3A:
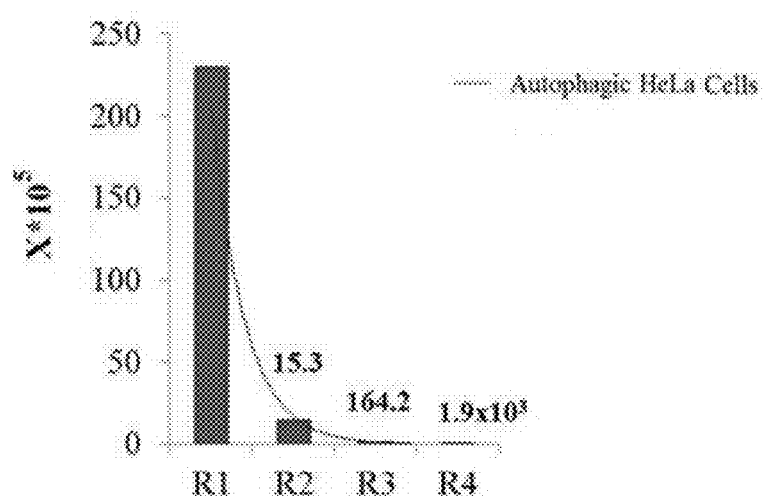
FIGS. 3A and 3B show the calculated tilter in the process of screening the phage library by the direct bio-panning method on HeLa cells (FIG. 3A) and MDA-MB-231 cells (FIG. 3B) in rounds R1, R2, R3, R4.
Figure 3B:
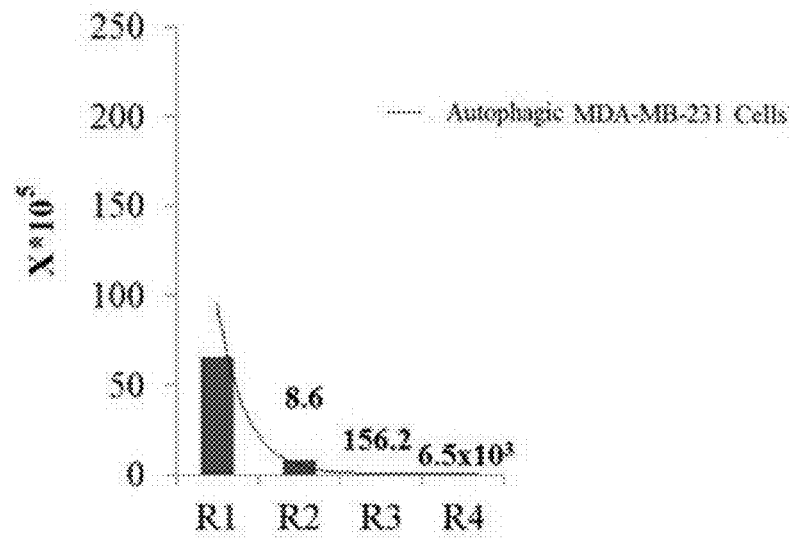

As described above, negative selection or subtraction process by culturing the phage library with rapamycin-untreated cells prior to culturing the phage library with rapamycin-treated cells was included in order to increase the selectivity of phage clones specific to autophagy cells. The present invention used a direct screening method to use all phage clones in the next round without amplification in contrast to classical phage amplification and phage enrichment methods. FIGS. 3A and 3B represent the phage titer in each round. Fold reduction of phage clones decreased to $1.9 \times 10^3$ fold (HeLa cells) and $6.5 \times 10^3$ fold (MDA-MB-231 cells), respectively, at 4 rounds. Sequence analysis was performed on a total of 90 clones from the third and fourth rounds (37 phage clones from HeLa cells, 53 phage clones from MDA-MB-231 cells).

<1-3> DNA and Amino Acid Sequence Analysis of a Phage Clone

The DNA inserts of each of the 90 clones collected in Example 1-2 were sequenced by an automated DNA sequencer (Genotech Inc., Daegeon, Korea) using −96 pIII primer (New England Biolabs) respectively. The amino acid sequences deduced from the nucleotide sequences were aligned using Clustal W program to find amino acid motifs shared between the consensus sequences or peptides. Some of these peptides were randomly selected and a BLAST search of the NCBI protein database was performed to investigate proteins with high homology to each peptide sequence.

<1-4> Selecting of Phage Clones

A phage clone with high specificity for binding to autophagy cells was selected through phage binding ELISA for autophagy cells. More specifically, For binding of each phage clone in vitro, cells were seeded at $2 \times 10^4$ cells/well in a 96-well culture plate and cultured in 80~90% confluence. And then cells were treated with rapamycin in serum-free medium for 4 hours, then washed with PBS and blocked with 1% BSA for 30 minutes at room temperature. The treated cells were then incubated with each phage clone ($1 \times 10^9$ pfu/well). The pool of a phage library was used as a control. After 1 hour incubation at 4° C. with a phage clone, the cells were washed again with PBS and fixed with 1% BSA (in DMEM). Next, HRP-conjugated anti-M13 phage monoclonal antibody (1:3000 dilution, NEB) was added to M13 phage and incubated at room temperature for one hour. The cells were washed three times with PBS, and the TMB substrate (100/well) was treated for 2-10 min for color development and the reaction was terminated by treatment with 2M $H_2SO_4$. The final color product was measured at 450 nm wavelength in microtitration plate reader (Sunrise, Tecan Austria) using a windows based program XFluor4.

Figure 4:
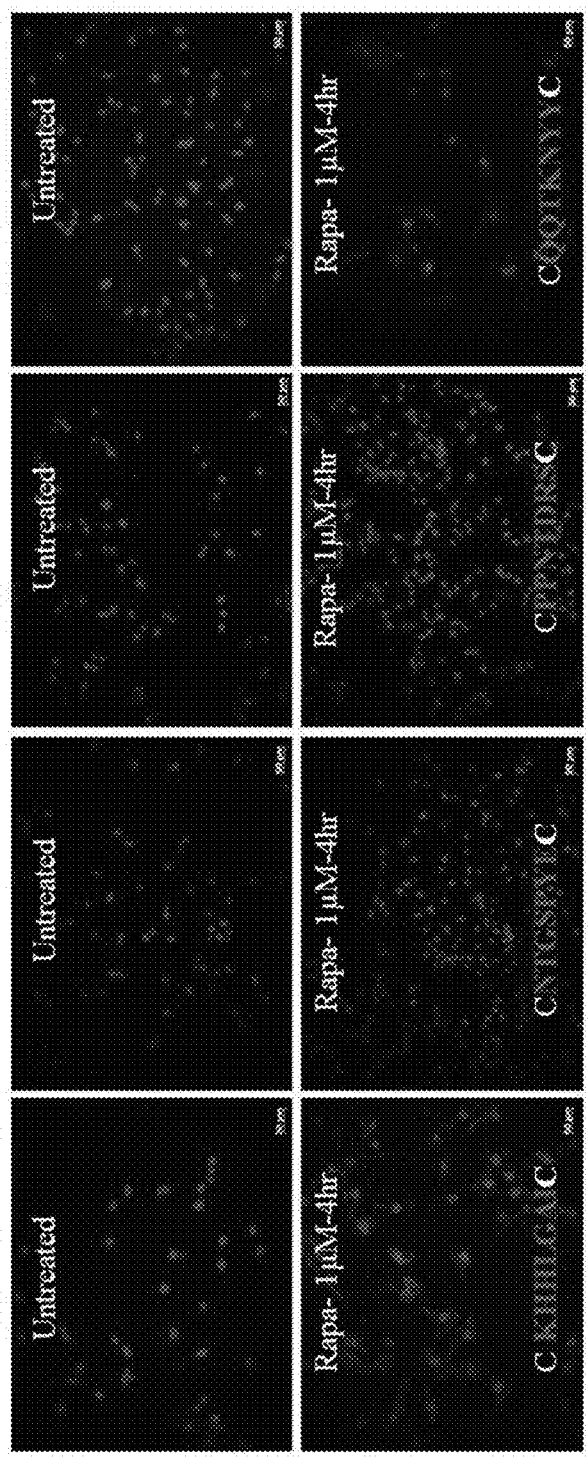
FIG. 4 shows the result of confirming that the four phage clones were specifically bound to autophagic cells through immunofluorescence staining (Rapa: rapamycin). SEQ ID NO: 1, SEQ ID NO: 3, SEQ ID NO: 4, and SEQ ID NO: 2 are respectively listed on the lower panels.

Further, after the phage clones selected for the rapamycin-treated cells were cultured as described above, immunofluorescent staining was performed using a mouse monoclonal antibody to M13 phage (mouse anti-M13 monoclonal antibody, diluted 1:3000) and Alexa 549-labeled antibody (Alexa 549-conjugated anti-mouse IgG antibody, abcam) against the mouse antibody as a secondary antibody in a conventional manner to confirm the attachment specificity and effect of the phage clones, and used for screening. Four phage clones were found to have high binding specificity to autophagy cells. The four peptide sequences of the clones is as follows; CKHHLGAIC (AtgPep-1, SEQ ID NO: 1), CQQTKNYYC (AtgPep-2, SEQ ID NO: 2), CNTGSPYEC: SEQ ID NO: 3 (AtgPep-3, SEQ ID NO: 3), CPPNTDRSC (AtgPep-4, SEQ ID NO: 4). FIG. 4 shows immunofluorescence staining observations of the clones of AtgPep-1 to AtgPep-4. It was confirmed that the phage clones displaying AtgPep-1 to AtgPep-4 specifically bind to autophagy cells respectively. In particular, it was confirmed that the phage clones specifically bind to the autophagy cells even in the initial (4 hr) autophagy state.

Example 2

Confirming the Binding Ability of the Peptide of the Present Invention to Autophagic Cells <2-1> Peptide Synthesis Peptides of the present invention in which Rhodamine B was conjugated to their N-terminus were produced by Peptron Co., Daegeon, Korea. In brief, each peptide was synthesized by the standard Fmoc methods and Rhodamine B was conjugated to the N-terminus of each peptide and purified by mass spectrometry.

<2-2> Identification of the Distinguishing Ability of the Peptide Against Apoptotic Cells It was examined whether the peptides of the present invention synthesized in Example <2-1> were distinguishable from apoptotic cells and specifically bound to autophagic cells only.

MDA-MB-231 cells treated with 10 ng of Trail, apoptotic drug, for overnight, then treated with FITC-conjugated ApoPep-1 (FITC labeled CQRPPR peptide; SEQ ID NO: 9) specifically targeting apoptotic cells or rhodamine B-conjugated AtgPep-1 to AtgPep-4. After fixing the cells, it was observed under a fluorescence microscope.

Figure 5:
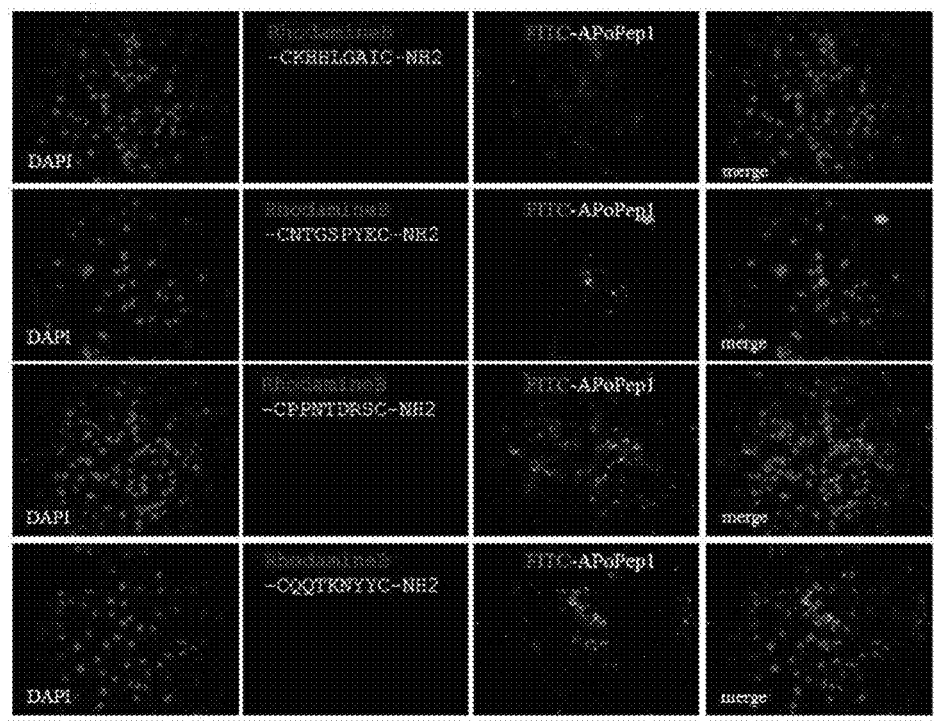
FIG. 5 shows the results of confirming that the peptides of the present invention labeled with rhodamine B do not bind to cells induced by apoptosis (FITTC-APoPep1: FITTC-labeled group treated with APoPep1, specifically binding in apoptotic cells only). SEQ ID NO: 1, SEQ ID NO: 3, SEQ ID NO: 4, and SEQ ID NO: 2 are respectively listed in the second column of panels.

As shown in FIG. 5, it was confirmed that AtgPep-1 to AtgPep-4 of the present invention did not bind to apoptotic cells.

<2-3> Confirmation of the Ability of the Inventive Peptide to Detect Autophagy Cells in the Early Stages of Autophagy Induction pEGFP-LC3-transfected MDA-MB-231 cells were cultured on an eight-chamber slide and were treated with EBSS (Earl's balanced salt solution) for 2 hours to induce autophagy. Cells were then washed with PBS and treated with 10 µmol/L of each solution of Rhodamine B-labeled AtgPep-1 to AtgPep-4 (provided in PBS diluted) and incubated at 4° C. for 1 hour. Then 1% BSA was treated at 4° C. for 1 hour. The cells were fixed with 4% paraformaldehyde for 5 minutes. The cells were then stained with 4V 6-diamidino-2-phenylindole (DAPI) and mounted on a fluorescence microscope (Zeiss, Oberkochen, Germany).

Figure 6:
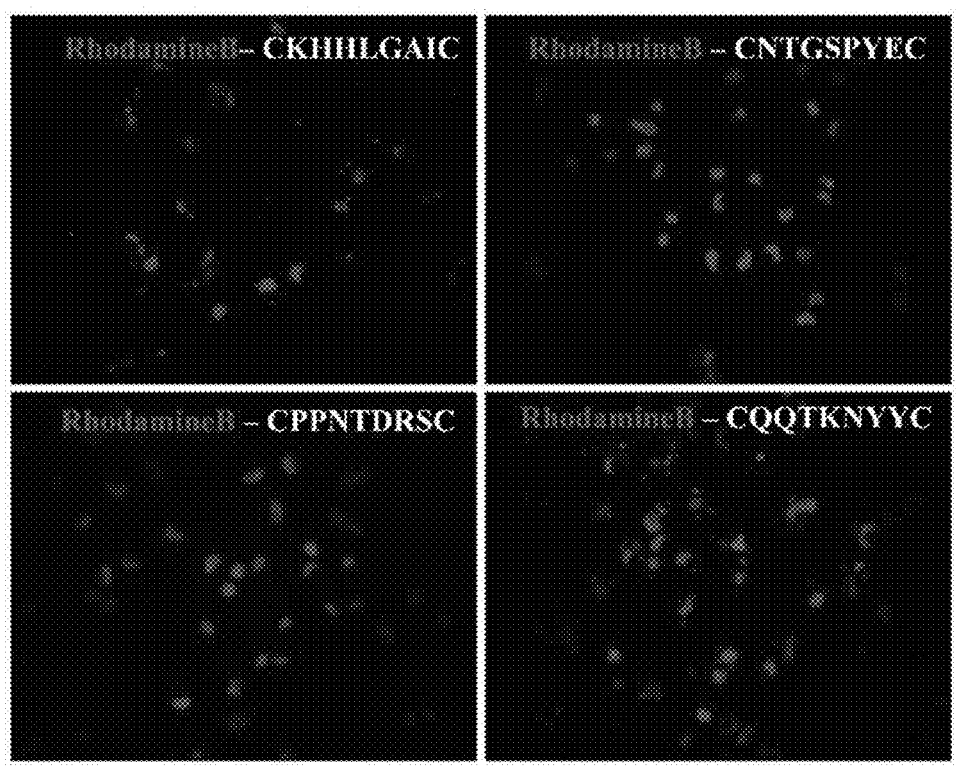
FIG. 6 shows the results of confirming that the peptides AtgPep-1 or AtgPep-4 of the present invention labeled with rhodamine B specifically bind early stage autophagy cells. SEQ ID NO: 1 and SEQ ID NO: 2 are respectively listed on the panels.

As shown in FIG. 6, AtgPep-1 (CKHHLGAIC; SEQ ID NO: 1) and AtgPep-2 (CQQTKNYYC: SEQ ID NO: 2) among the peptides of the present invention showed strong fluorescence signals. As a result, it was confirmed that the peptides of the present invention were able to detect initial autophagy as in Example 1-4. FIGS. 7A and 7B show the binding of rhodamine-labeled AtgPep-1 and AtgPep-2 to MDA-MB-231 cells (single cell) induced by autophagy, confirming that the peptide of the present invention was bound to the cell membrane of the autophagy cell.

Figure 8:
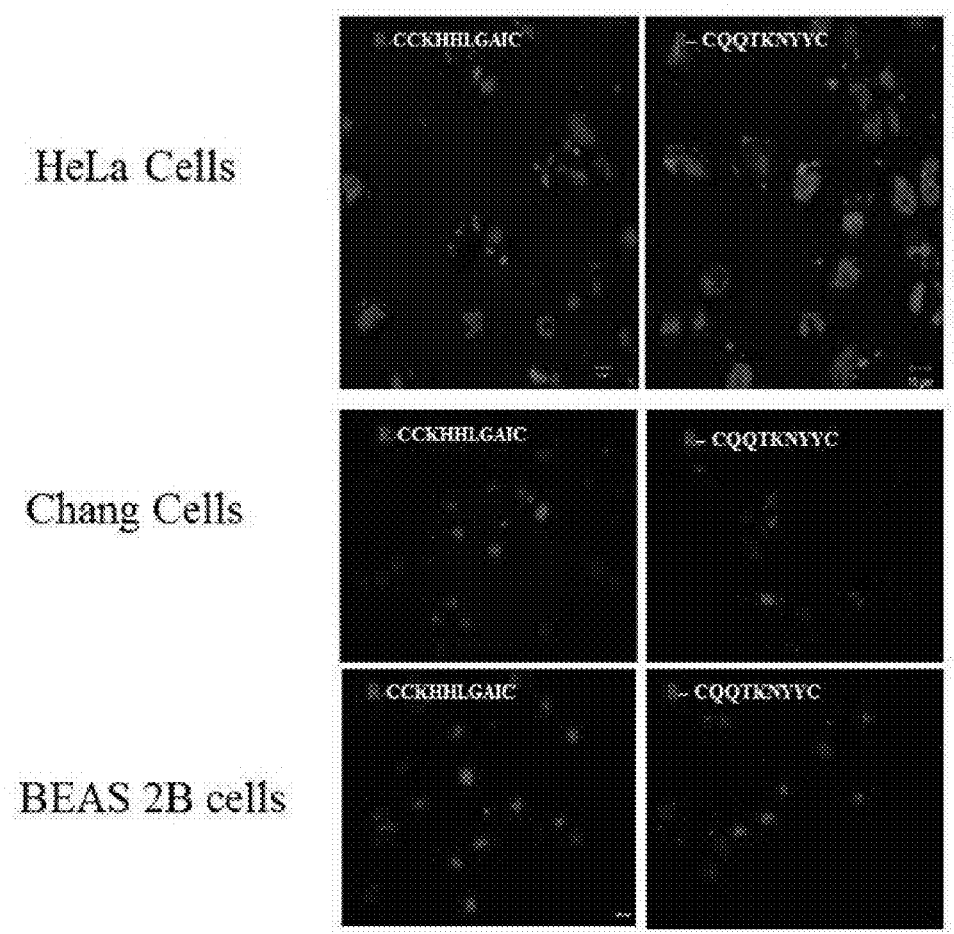
FIG. 8 is a single cell image showing that the peptide of the present invention is bound to the cell membrane in autophagy-induced HeLa cells, Chang cells, and BEAS 2B cells (RB: rhodamine B labeled). SEQ ID NO: 1 and SEQ ID NO: 2 are respectively listed on each panel in the first column and second column.

In order to verify that the peptide of the present invention acts also on other tissues or cells other than the MDA-MB-231 cell line, autophagy was induced in several kinds of cells (derived from different tissues) and their detection ability was confirmed using AtgPep-1 (CKHHLGAIC; SEQ ID NO: 1) and AtgPep-2 (CQQTKNYYC: SEQ ID NO: 2) which represent particularly high signals among AtgPep-1 to AtgPep-4. The experimental method is the same as described above. As a result, as shown in FIG. 8, it was confirmed that the peptides, AtgPep-1 and AtgPep-2, were specifically targeted to autophagy cells regardless of cell types although AtgPep-1 and AtgPep-2 of the present invention have different signal intensities depending on the autophagy intensity induced in each cell line of HeLa cell, Chang cell and BEAS-2B cell.

<2-4> Identification of Autophagy-Specific Targets and Binding in Animal Models

As an experiment for monitoring and imaging autophagy using a peptide probe, tumor cells were transplanted into immunodeficient nude mice to grow tumors, and animal models for experiments were constructed. The MDA-MB-231 cell ($10^6$ cells), which was verified in the results of FIGS. 7A and 7B of the present invention, was injected into the femoral region of the nude mouse, and it was confirmed that the size of the tumor was 80 mm$^3$ after 10 days. In order to induce autophagy, rapamycin was injected intraperitoneally into each mouse in an amount of 1.5 mg per kg of the mouse. Two hours after the injection of rapamycin, AtgPep-2 (CQQTKNYYC: SEQ ID NO: 2) of the present invention, labeled with flamma 675 (=FPR675, Bioact Co., Korea), a near-infrared fluorescent (NIRF) was administered to each mouse (N=5 To 7) via tail vein at a final 50 µM concentration/mouse, while being allowed to circulate along the blood for 2 hours to obtain optical and fluorescence imaging at 2 hours, 4 hours, and 5 hours after the administration of the peptide. As a control, CNSSSVDKC peptide (Control, SEQ ID NO: 10) labeled with flamma 675 was injected at the same concentration and method. NIRF imaging signals were scanned and acquired using an IVIS imaging system (Caliper Life Sciences, Massachusetts, USA).

Figure 9:
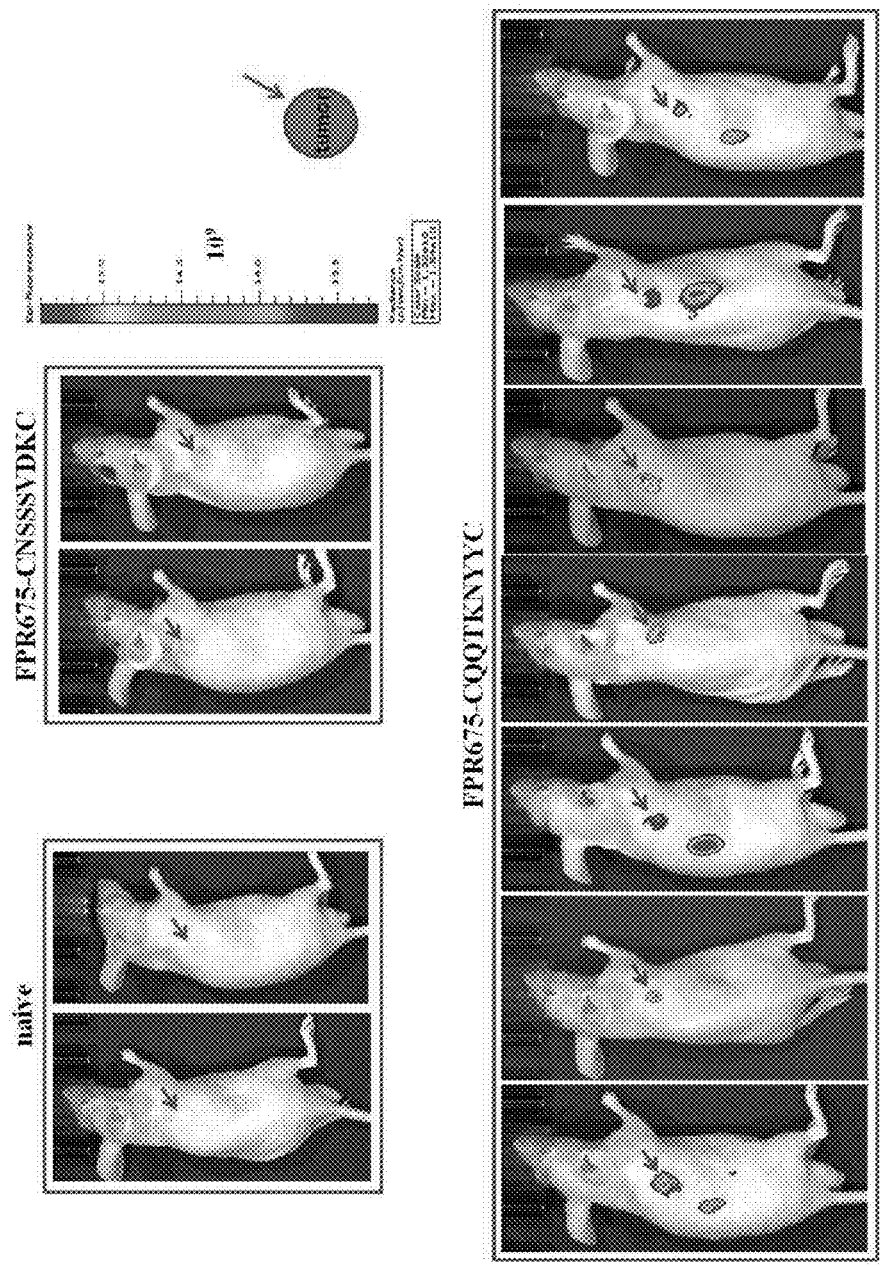
FIG. 9 shows the fluorescence images of the near-infrared fluorescence representing that the peptide of the present invention is targeted to a site where autophagy has occurred in tumor tissue in vivo after the autophagy was induced by administering rapamycin to a tumor animal model (CNSSSVDKC (SEQ ID NO: 10) a control group injected with CNSSSVDKC peptide, CQQTKNYYC: SEQ ID NO: 2 a group injected with CQQTKNYYC, SEQ ID NO: 2 peptide (AtgPep-2)).

As shown in FIG. 9, when the peptide AtgPep-2 (CQQTKNYYC: SEQ ID NO: 2) of the present invention was compared with the fluorescence imaging obtained in the mice injected with the control peptide (CNSSSVDKC) 4 to 5 hours after the peptide injection, it was confirmed that the peptide AtgPep-2 (CQQTKNYYC: SEQ ID NO: 2) of the present invention was targeted (indicated by an arrow) to the tumor at a significantly higher level after autophagy induction.

The target signal in the tissue was observed with a microscope to confirm whether the result of the image signal shown in FIG. 9 of the present invention was the result of the peptide target following autophagy induction in the tumor. After five hours of the peptide injection, the image were acquired. Then the mice were sacrificed and the tumors were separated and frozen sections of tissues were prepared. Six µm-thickness tumor frozen sections were stained with DAPI for nuclear staining and immunostained with LC3 antibody for autophagy induction. The signal of flamma 675 (FPR675) dye, LC3 and DAPI were observed as red, green and blue under a microscope, respectively.

As shown in FIG. 10, five hours after the peptide injection, the target signal in the tumor tissue injected with the peptide AtgPep-2 (CQQTKNYYC: SEQ ID NO: 2) of the present invention was significantly higher than that in the control peptide injection group as the result of the image observed in vivo. On the other hand, as a result of LC3 immunostaining, it was confirmed that autophagy was induced well in both the AtgPep-2 (CQQTKNYYC: SEQ ID NO: 2) peptide injection group and the control peptide (CNSSSVDKC) injection group. That is, in the control peptide injection group, autophagy was induced but the target signal was not present, whereas the target signal of the AtgPep-2 peptide was confirmed. In addition, the result of the biomedical image shown in FIG. 9 confirms that the target of the peptide occurred because the actual autophagy was induced in the tumor.

INDUSTRIAL APPLICABILITY

As described above, the present invention relates to an autophagic cell-targeted peptide and its use. More particularly, the present invention relates to a polypeptide comprising an amino acid sequence represented by the general formula (I) and specifically binding to an autophagic cell and a composition for detecting autophagic cells comprising the same as an active ingredient, a drug delivery composition containing the same as an active ingredient, and a composition for imaging comprising the same as an active ingredient.

The peptide of the present invention specifically binds to the cell membrane of autophagic cells and can be applied to various kinds of tissues and cells. Since its detection and imaging effect of autophagy is remarkable in vitro and in vivo, it is highly likely to be industrially applicable.

What is claimed is:

1. A polypeptide that specifically binds to an autophagic cell, consisting of an amino acid sequence represented by the following general formula (I);

(amino-terminus-C-X1-X2-X3-X4-X5-X6-X7-C-carboxy-terminus)     (I)

wherein C is cysteine,

X1 is any one amino acid selected from the group consisting of lysine, glutamine, asparagine and proline;

X2 is any one amino acid selected from the group consisting of histidine, glutamine, threonine and proline;

X3 is any one amino acid selected from the group consisting of histidine, threonine, glycine and asparagine;

X4 is any one amino acid selected from the group consisting of leucine, lysine, serine and threonine;

X5 is any one amino acid selected from the group consisting of glycine, asparagine, proline and aspartic acid;

X6 is any one amino acid selected from the group consisting of alanine, tyrosine and arginine; and X7 is any one amino acid selected from the group consisting of isoleucine, tyrosine, glutamic acid and serine.

2. The polypeptide according to claim 1,
wherein X1 is lysine or glutamine;
X2 is histidine or glutamine;
X3 is histidine or threonine;
X4 is leucine or lysine;
X5 is glycine or asparagine;
X6 is alanine or tyrosine, and
X7 is isoleucine or tyrosine.

3. The polypeptide according to claim 1, wherein the polypeptide is an amino acid sequence selected from the group consisting of SEQ ID NO: 1 to SEQ ID NO: 4.

4. A composition comprising the polypeptide of claim 1 as an active ingredient.

5. A composition comprising as an active ingredient a polypeptide comprising an amino acid sequence represented by the following general formula (I);

(amino-terminus-C-X1-X2-X3-X4-X5-X6-X7-C-carboxy-terminus) (I)

wherein C is cysteine,

X1 is any one amino acid selected from the group consisting of lysine, glutamine, asparagine and proline;

X2 is any one amino acid selected from the group consisting of histidine, glutamine, threonine and proline;

X3 is any one amino acid selected from the group consisting of histidine, threonine, glycine and asparagine;

X4 is any one amino acid selected from the group consisting of leucine, lysine, serine and threonine;

X5 is any one amino acid selected from the group consisting of glycine, asparagine, proline and aspartic acid;

X6 is any one amino acid selected from the group consisting of alanine, tyrosine and arginine; and X7 is any one amino acid selected from the group consisting of isoleucine, tyrosine, glutamic acid and serine; and wherein the polypeptide is labeled with any one selected from the group consisting of a chromogenic enzyme, a radioisotope, a chromophore, a luminescent material, a fluorescer, a magnetic resonance imaging material, superparamagnetic particles, and ultrasmall superparamagnetic particles.

* * * * *

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Artificial Amino acid sequence of AtgPep-1

<400> SEQUENCE: 1

Cys Lys His His Leu Gly Ala Ile Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Artificial Amino acid sequence of AtgPep-2

<400> SEQUENCE: 2

Cys Gln Gln Thr Lys Asn Tyr Tyr Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Artificial Amino acid sequence of AtgPep-3

<400> SEQUENCE: 3

Cys Asn Thr Gly Ser Pro Tyr Glu Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Artificial Amino acid sequence of AtgPep-4

<400> SEQUENCE: 4

Cys Pro Pro Asn Thr Asp Arg Ser Cys
1               5

<210> SEQ ID NO 5
<211> LENGTH: 27
<212> TYPE: DNA
<213> ORGANISM: Artificial Sequence
<220> FEATURE:
<223> OTHER INFORMATION: Artificial nucleotide sequence of AtgPep-1

<400> SEQUENCE: 5
tgtaagcatc atctgggtgc gatttgc                                      27
```

```
<210> SEQ ID NO 6
<211> LENGTH: 27
<212> TYPE: DNA
<213> ORGANISM: Artificial Sequence
<220> FEATURE:
<223> OTHER INFORMATION: Artificial nucleotide sequence of AtgPep-2

<400> SEQUENCE: 6
tgtcagcaga cgaagaatta ttattgc                                           27

<210> SEQ ID NO 7
<211> LENGTH: 27
<212> TYPE: DNA
<213> ORGANISM: Artificial Sequence
<220> FEATURE:
<223> OTHER INFORMATION: Artificial nucleotide sequence of AtgPep-3

<400> SEQUENCE: 7
tgtaatactg gttcgcctta tgagtgc                                           27

<210> SEQ ID NO 8
<211> LENGTH: 27
<212> TYPE: DNA
<213> ORGANISM: Artificial Sequence
<220> FEATURE:
<223> OTHER INFORMATION: Artificial nucleotide sequence of AtgPep-4

<400> SEQUENCE: 8
tgtccgccga atactgatcg ttcgtgc                                           27

<210> SEQ ID NO 9
<211> LENGTH: 6
<212> TYPE: PRT
<213> ORGANISM: Artificial Sequence
<220> FEATURE:
<223> OTHER INFORMATION: Artificial Amino acid sequence of ApoPep-1

<400> SEQUENCE: 9

Cys Gln Arg Pro Pro Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Artificial Amino acid sequence of Control

<400> SEQUENCE: 10

Cys Asn Ser Ser Ser Val Asp Lys Cys
1               5
```